(12) United States Patent
Fröhlich et al.

(10) Patent No.: US 6,516,046 B1
(45) Date of Patent: Feb. 4, 2003

(54) EXACT PATIENT POSITIONING BY COMPAIRING RECONSTRUCTED X-RAY IMAGES AND LINAC X-RAY IMAGES

(75) Inventors: Stephan Fröhlich, Aschheim (DE); Cornel Schlossbauer, Krailing (DE); Andreas Blumhofer, München (DE)

(73) Assignee: BrainLAB AG, Kirchheim/Heimstetten (DE)

( * ) Notice: Subject to any disclaimer, the term of this patent is extended or adjusted under 35 U.S.C. 154(b) by 0 days.

(21) Appl. No.: 09/668,821

(22) Filed: Sep. 22, 2000

(30) Foreign Application Priority Data

Nov. 4, 1999 (DE) .......................................... 199 53 177

(51) Int. Cl.[7] .................................................. A61N 5/10
(52) U.S. Cl. .............................. 378/65; 378/68; 378/205
(58) Field of Search .............................. 378/65, 68, 20, 378/205, 4, 901, 98.12

(56) References Cited

U.S. PATENT DOCUMENTS

| | | | |
|---|---|---|---|
| 5,622,187 A | 4/1997 | Carol | ......................... 128/897 |
| 5,754,622 A | * | 5/1998 | Hughes ........................ 378/65 |
| 5,901,199 A | | 5/1999 | Murphy et al. ............... 378/65 |
| 6,125,164 A | * | 9/2000 | Murphy et al. ............... 378/65 |
| 6,269,143 B1 | * | 7/2001 | Tachibana .................... 378/65 |

FOREIGN PATENT DOCUMENTS

| | | |
|---|---|---|
| DE | 44 18 216 A1 | 11/1995 |
| DE | 197 28 788 A1 | 1/1999 |

* cited by examiner

Primary Examiner—Robert H. Kim
Assistant Examiner—Jurie Yun
(74) Attorney, Agent, or Firm—Renner, Otto, Boisselle & Sklar, LLP

(57) ABSTRACT

A method for exact positioning of a patient for radiotherapy or radiosurgery comprising the following steps: a) pre-positioning the patient relative to a linear accelerator, b) producing at least one X-ray image of the patient or one of his/her body parts in the vicinity of the radiation treatment target, c) mapping the X-ray image, d) generating at least one reconstructed image from a three-dimensional set of patient scanning data corresponding to said X-ray image, especially isocentrically, e) superimposing the reconstructed image and the X-ray image, and detecting the positional error electronically or computer-controlled on the basis of specific landmarks in both images, and f) correcting the position of the patient on the basis of the detected positional error.

33 Claims, 4 Drawing Sheets

EXACT PATIENT POSITIONING BY COMPAIRING RECONSTRUCTED X-RAY IMAGES AND LINAC X-RAY IMAGES

BACKGROUND OF THE INVENTION

1. Technical Field

The present invention relates to a method for exact positioning of a patient for radiotherapy or radiosurgery. The present invention relates furthermore to a method of three-dimensionally mapping an X-ray image.

2. Description of Related Art

Major advances have been made recently in dose planning in the fields of radiotherapy and radiosurgery. Attempts are being made to bring treatment ever nearer to radiosurgical dosing, i.e. to work with higher radiation doses in fewer sessions, preferably only in a single session concentrated to a target volume, for instance, a tumor. Although engineering the dosage is relatively successful, as mentioned, the fact that the patient or the body site to be irradiated can only be positioned relatively inaccurately is often an obstacle to high dosage applications administered in a single or a few fractions. This is why, in most cases, recourse is made to conventional fractionated radiotherapy involving repeat application in low dosage so as to avoid greater damage to healthy tissue.

To improve positioning, currently, a very inaccurate "manual" method is used, in which an X-ray image of the patient's body part is produced in a linear accelerator. This image is compared to a reference radiograph, previously obtained at the simulator (an X-ray unit, the geometry of which is identical to that of the linear accelerator). The X-ray image and the simulator image are then compared by the physician, for example, on a light box, the positioning error between the actual position of the patient and the desired position is measured with a ruler and the patient is moved accordingly. At the most, the physician may also have a center beam reticule and/or the contour of the outer boundaries of the site available in both images as a guideline. The boundaries of the site may be defined e.g. by blocks of lead or driven beam blinds. Even when comparing DDRs (virtual "simulator images" detected from a set of three-dimensional image data) instead of real simulator images, this method remains unchanged.

Disadvantageously, this kind of patient positioning is already inaccurate for the following reasons:

The images are projective and thus not true-to-scale (no uniform image scale exists). "Manual" reading of the necessary correctional shift is inaccurate.

A three-dimensional correctional shift from two-dimensional images without computer assistance is possible only to a limited degree and requires a lot of experience.

Known from U.S. Pat. No. 5,901,199 is an iterative method of aiming radiation therapy beams at a treatment target using diagnostic computer tomography data, with the aid of which a plurality of digitally reconstructed radiographs (DRRs) is generated. These DRRs are continually generated and compared to an X-ray image produced in situ until one is found which is a suitable match. With the aid of the data obtained thereby, the position of the treatment unit or radiation beam is corrected so that the beam strikes the target of treatment.

The disadvantage in this method is the high computation requirement since, to start with, the DRRs have to be generated at random, and a lot of them need to be compared to the actual X-ray image. In particular, the method requires finding a "smart" algorithm to approximate the DRR matching each body segment and for each patient in a reasonable time period.

SUMMARY OF THE INVENTION

An object of the present invention is to propose a method for the exact positioning of a patient for radiotherapeutical or radiosurgical applications, which obviates the above-cited disadvantages of the prior art. It is in particular the intention to achieve a very precise repositioning of the patient in a simple manner and in a short time, and automatically where possible.

This object is achieved in accordance with the invention by a method for the exact positioning of a patient for radiotherapeutical/surgical applications comprising the steps:

a) pre-positioning the patient relative to a linear accelerator, b) producing at least one X-ray image of the patient or one of his body parts in the vicinity of the radiation treatment target, c) mapping the X-ray image, d) generating at least one reconstructed radiograph from a three-dimensional set of patient scanning data corresponding to said X-ray image, especially isocentrically, e) superimposing the reconstructed image and the X-ray image, and detecting the positional error electronically or computer-controlled on the basis of specific landmarks in both images, and f) correcting the location of the patient on the basis of the detected positional error.

It is of advantage that repositioning as proposed in accordance with the invention is a relatively quick way of obtaining a very precise target radiation. The electronic or computer-assisted detection of the positional error enhances accuracy quite considerably as compared to the "manual" method. Mapping the X-ray image permits including this input data with sufficient accuracy in the analysis, so that errors and delays in the repositioning are also avoided from this end.

Pre-positioning occurs preferably in a method in accordance with the invention by means of a computer-controlled and camera-controlled navigation and tracking system with the aid of artificial, in particular reflecting, marker arrangements on the patient and the treatment units. Such a navigation and tracking system is able to handle all tasks involved in position sensing during implementation of the method in accordance with the invention and outputting the corresponding information for example on a computer display.

However, pre-positioning the patient may also be carried out by means of skin markers on the patient, natural landmarks or laser markings.

In principle, it should suffice to produce simply one X-ray image and to generate a corresponding reconstructed image. However in preferred embodiments of the method in accordance with the invention, at least two or more X-ray images and a corresponding number of reconstructed images are generated from different directions, and each are analyzed by comparison to enable any tilting of the patient or of the patient carrier to be taken into account in computation.

The X-ray image may be advantageously produced using a linear accelerator. Such X-ray images are called EPID images(Electronic Portal Imaging Device images), and the corresponding images can be produced on a flat panel (e.g. amorphous silicon) on an X-ray film or on any other two-dimensional imaging medium.

On the other hand, it is, of course, possible to produce the X-ray images by a separate X-ray source, e.g. with the aid of two X-ray sources, secured overhead, which generate sequential (electronic) X-ray images on a detector (e.g. amorphous silicon). If the detector cannot be positioned in the isocenter for various reasons (e.g. rotation of the gantry), an offset needs to be taken into account, both in approximate positioning and in error correction.

Quite generally, the X-ray image may be produced on an image amplifier or detector, in particular on the amorphous silicon stated since, by using amorphous silicon (flat panel) distortions are minimized. However, of course, it is also possible to use a scanned X-ray film. The X-ray image may be produced either by an imaging system integrated in the linear accelerator or by a separate X-ray unit.

In an embodiment of the method in accordance with the invention, superimposing the X-ray image and the reconstructed radiograph is effectuated by marking and interleaving as controlled by the user on a computer display (e.g. using mouse, keyboard, touchscreen, joystick, etc). On the other hand, superimposing of the X-ray image and of the reconstructed image may also occur by computer-controlled automatic image fusion.

In preferred embodiments of the method in accordance with the invention, the reconstructed image or reconstructed images is/are generated as digitally reconstructed radiographs (DRRs)

digitally composited radiographs (DCRs)

MIP images or as any two-dimensional image reconstruction from a set of three-dimensional patient scan data.

The position of the patient is corrected in accordance with the invention advantageously by moving the patient table, in particular automatically operated and corrected by a computer-controlled and camera-controlled navigation and tracking system with markers on the patient and/or on the patient table. In principle, it is also possible to correct the position of the patient by operating the table manually.

In accordance with a preferred embodiment of the method in accordance with the invention, in the steps c) and d) cited above, a plurality of reconstructed images is generated, which are then superimposed and compared to the mapped X-ray image, electronically or computer-controlled, until a reconstructed image is found which corresponds to the X-ray image, with the aid of which the positional error is then detected.

In this case, there is no need for isocentric reconstructed images since it is possible to increasingly approximate the desired reconstructed image by computer approximation procedures (algorithms). This embodiment is particularly of advantage since it permits a wider scope in patient pre-positioning. By using a mapped X-ray image, finding the corresponding reconstructed image is quicker and more precise.

The invention relates furthermore to a method of three-dimensionally mapping an X-ray image comprising the steps:

producing an X-ray image of the patient, detecting the three-dimensional position of the X-ray unit while producing the X-ray image.

inserting markers in a predetermined or specific position relative to the X-ray source in the beam path thereof whilst producing the X-ray image, and computing, from the geometry of the X-ray unit and from the position of the markers in the X-ray image, the precise three-dimensional imaging situation of the X-ray image.

By means of the above method in accordance with the invention, it is now possible to precisely determine the three-dimensional position of an X-ray image. This is particularly important when this X-ray image is used as an input parameter for further mapping and positioning, since this already enables this input value to be defined precisely mapped and correctly. During image formation at a linear accelerator, the position of the image amplifier or of the film on its holder is often not 100% fixed relative to the radiation source and relative to the isocentric beam. An error of this kind can be excluded by mapping each individual X-ray image.

In this arrangement, it is now possible to determine the three-dimensional position of the X-ray source and/or of the image receiver, as well as of a patient carrier, by means of a computer-controlled and camera-controlled navigation and tracking system with markers. Furthermore, detecting the three-dimensional position of the X-ray source and/or image receiver may also be done via scaled detection means on these units.

In an embodiment of the mapping method, the X-ray image is produced by a linear accelerator for radiotherapy/radiosurgery with an image receiver, a carrier for the markers being fixedly positioned in front of the radiation source. These markers appear on the X-ray image to then make it possible to precisely compute the three-dimensional imaging situation of the X-ray image from their known distance away from the radiation source as well as from their known marker geometry.

Advantageously, a linear accelerator with a leaf collimator is used in front of the radiation source, the markers being formed by collimator leafs driven into the radiation path to a specific degree. In this arrangement, the zone of the leaf collimator may either already have the radiation shape or it may be specially shaped for mapping, the leafs being extended asymmetrical only edgewise so as not to detriment the image. Generally, the distances between the radiation source and the marker carrier or leaf collimator are fixed and known. If need be, however, a calibration with a phantom may provide even more precise values.

In accordance with the invention, it is of course possible, and preferably also provided, to use the method described for three-dimensionally mapping an X-ray image, utilizing an X-ray image within the scope of the method described for the exact positioning of a patient.

BRIEF DESCRIPTION OF THE DRAWINGS

The invention will now be detailed with reference to the attached drawings in which.

DETAILED DESCRIPTION

Figure 1A:
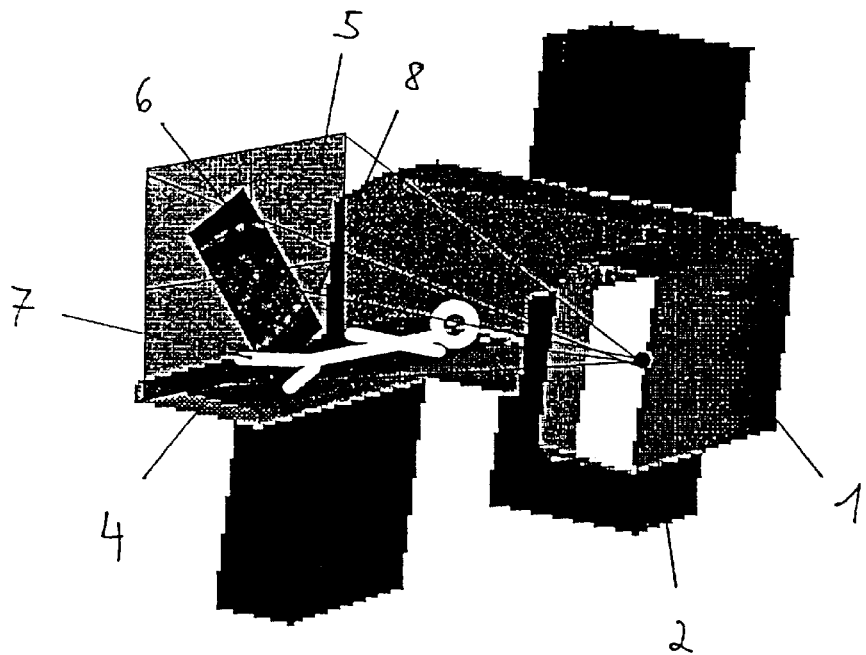
FIGS. 1a+1b depict two different imaging situations for X-ray images produced with a linear accelerator.
Figure 1B:
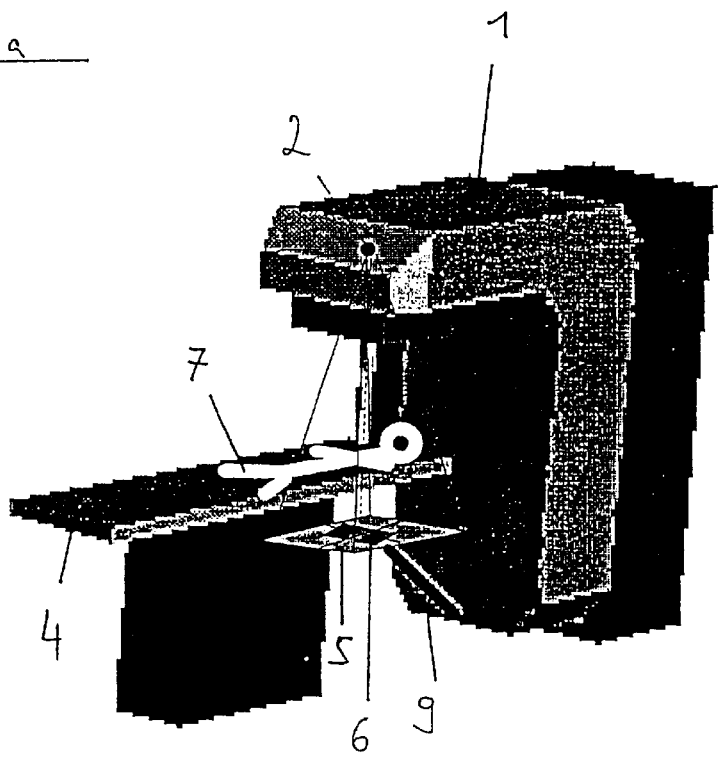

In FIGS. 1a and 1b, it is illustrated how X-ray images are produced from two different directions with the aid of a linear accelerator. The linear accelerator comprises a gantry 1, which is mounted swiveling and in the upper part of which the radiation source 2 is arranged. As evident from FIG. 1b, a support 9 is secured for opening out on the lower part of the gantry 1, the support comprising the imaging system 5, on which the image receiver is arranged. Such an image receiver may be simply an X-ray film (as shown), however, it may also be a flat panel (e.g. of amorphous silicon) or an image amplifier. The isocentric beam 8 from the radiation source 2 passes through the patient 7 onto the imaging system, an X-ray image thereby being produced on the X-ray film 6. For this purpose, the patient 7 is already pre-positioned as best as possible with the aid of the patient table 4, which can be traveled by means of motors (not shown). Pre-positioning may be effectuated with the aid of a known tracking system and markers applied to the patient or to the patient table.

For the embodiment of the invention represented here, as shown in FIGS. 1a and 1b, two X-ray images are produced roughly at right-angles of the gantry.

Figure 2:
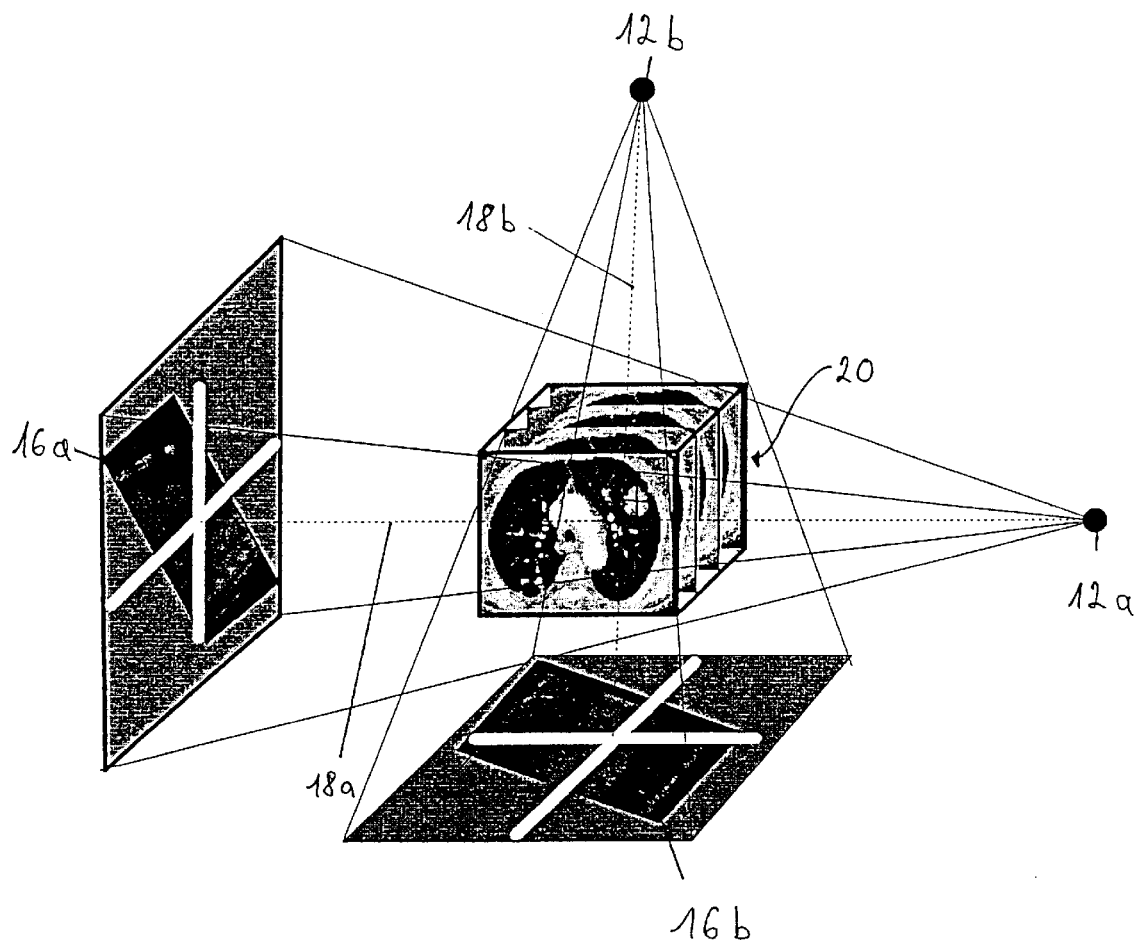
FIG. 2 is a schematic illustration of generation of two reconstructed images corresponding to the images in FIGS. 1a and 1b.

In FIG. 2, it is illustrated schematically how two correspondingly reconstructed images are generated. For this purpose, a computer tomography scan data set, generated previously from the patient, is used. In FIG. 2, this data set is represented by a sequence of section images 20. Using the known positioning data of the radiation source 2 (see FIGS. 1a and 1b), corresponding reconstructed X-ray images 16a and 16b are generated on the basis of the scanned data. The isocentric beams are given the numbers 18a and 18b.

Input data for generating the reconstructed images, also referred to in the following as DRRs (Digital Reconstructed Radiographs), are, for one thing, the positions of the radiations sources 12a and 12b. As the second input size, the three-dimensional arrangement of the plane, in which the X-ray image is produced, needs to be specified, i.e. both as regards the distance to the radiation source and as regards its tilt. In other words, the "virtual" X-ray films 16a and 16b need to be arranged precisely in the same way as the films 6 of the actual X-ray image so that the images can be compared. For this to occur, the X-ray images 6 from the in-situ (actual) radiograph (FIGS. 1a and 1b) need to be mapped, i.e. precisely defined as regards their distance and their tilt relative to the radiation source, which will be clarified in more detail later. As the third input size, the position of the target point in the three-dimensional data set needs to be known.

When the plane of the X-ray image and the direction of the central beam (position of the radiation source) are precisely known in the actual radiograph (FIGS. 1a and 1b) in situ, then the corresponding DRRs can be exactly reconstructed and assigned.

With the aid of FIGS. 3 and 4 it will now be described how the X-ray image produced in situ (FIGS. 1a and 1b) is mapped as regards its distance and its tilt relative to the radiation source.

Such a mapping is necessary, particularly since the position of the imaging system 5 and of the folding-out support 9, relative to the radiation source 2, cannot be regarded as being fixed for mechanical reasons (wobble, inaccurate hinging mechanism). Even if this position were to alter by only a few millimeters, this may result in undesired, faulty beaming. This is why in accordance with the invention in producing each X-ray image, its three-dimensional arrangement is determined to then be able to reconstruct the corresponding DRR in precisely the same plane.

Figure 3:
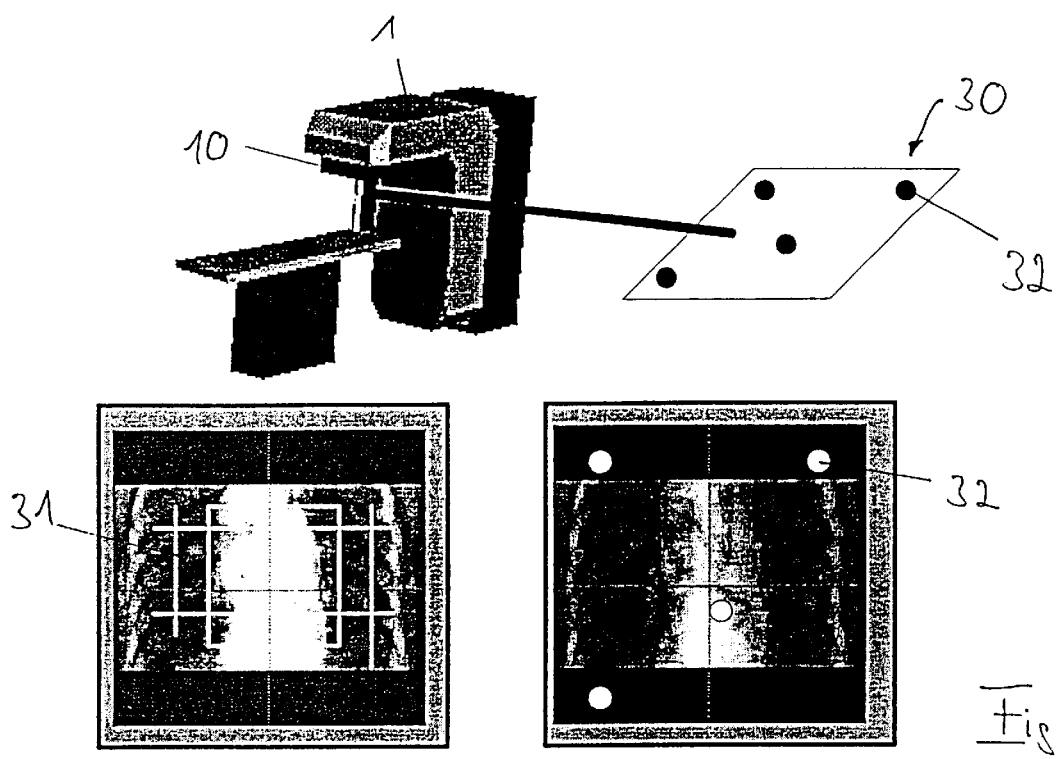
FIG. 3 illustrates introducing a marker carrier in an insert at the linear accelerator as well as two examples of marker geometries.
Figure 4:
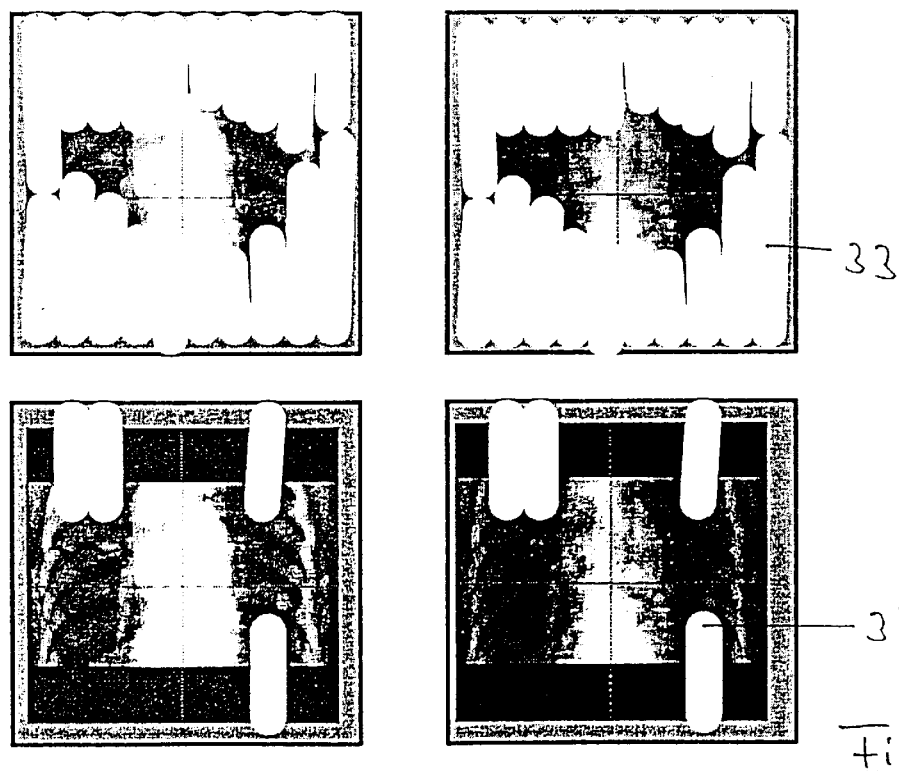
FIG. 4 depicts X-ray images, in which collimator leafs are imaged as markers.

The upper drawing in FIG. 3 schematically depicts an insert 30, provided with markers 33, and which is inserted into the radiation path in a mount 10 on the gantry 1 defined for this purpose. The insert 30 carries either circular markers 32 or line markings 31, and, in the X-ray image produced, these markers take the form as evident from the two lower illustrations in FIG. 3. From the distance and the distortion of the geometry of the markers 32 or lines 31, it can then be determined by simple geometry means at what distance the X-ray image was taken and its tilt at the time. The X-ray image obtained in situ is thus precisely mapped and with the aid of this data DRRs can be generated in precisely the same plane, as has already been explained above with reference to FIG. 2.

In a further embodiment of the method in accordance with the invention, the markers necessary for mapping are not generated by an additional insert, but by a leaf collimator, which for shaping the treatment beam is, in many cases, arranged in the radiation path of the linear accelerator. Such leaf collimators feature leafs which can be driven into the radiation path to thereby limit a beaming site in accordance with the outer form of the lesion to be radiated, so as to protect surrounding healthy tissue. Such beaming sites limited by advanced leafs 33 are evident in the two upper illustrations of FIG. 4.

However, it is also possible in accordance with the invention to make use of such driveable leafs as markings for mapping the X-ray image. For this purpose, as evident from the two lower illustrations shown in FIG. 4, individual leafs 34 are inserted into the image zone during production of the X-ray image. Distance and arrangement of these leafs 34 relative to the radiation source are also known so that from the projections onto the X-ray image, the same as with the separate markings 31 or 32 (FIG. 4), the three-dimensional position, i.e. tilt and spacing of the X-ray image produced can be determined. To avoid interfering with the image excessively, leafs are inserted merely in the periphery of the image asymmetrically.

Figure 5:
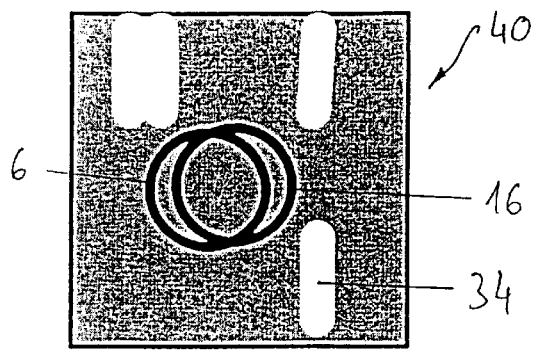
FIG. 5 is an illustration of a superimposition of an X-ray image and a reconstructed image.

Since the X-ray image produced in situ has been totally mapped and each of the DRRs could be generated in exactly the same plane, the images generated by these two methods may be directly compared. FIG. 5 shows a schematic representation in which two such images, namely the X-ray image produced in situ and the corresponding DRR, are superimposed. To make for a better demonstration, rings have been selected to represent the image objects, whereas usually bone structures, for example, would be seen. In FIG. 5, it is evident that the two images of the ring, namely the X-ray image, obtained in situ and identified by the reference numeral 6, and the image obtained from the DRR and identified by the reference numeral 16, are out of alignment to one another. This misalignment is a result of the still relatively inaccurate pre-positioning. The misalignment of the two rings to one another in at least one plane, preferably however in several planes (for two or more X-ray images or DRRs of different directions) is then determined with the aid of computer-controlled image processing (fusion) or manually, and the patient can be repositioned in accordance with the determined misalignment. This is preferably effectuated automatically via the motors for driving the patient table 4 (FIG. 1a or 1b). After this repositioning, the patient is then precisely located in such a position in which the treatment beam exactly targets the target for treatment, and treatment can commence.

It is to be noted that the two images, when superimposed, may also be marked manually, for example, also on a computer display, and interleaved until the images match in all planes. The image contents, which are superimposed, are mostly bone shadows in X-ray images. However, at this point, it must be said that, in principle, other scanning methods may be used with the principle of the present invention, for example, in the use of core spin tomography images, which, in themselves, provide relatively good images of the treatment site, so that the positional error can be determined to advantage by determining the misalignment of the treatment target itself.

Figure 6:
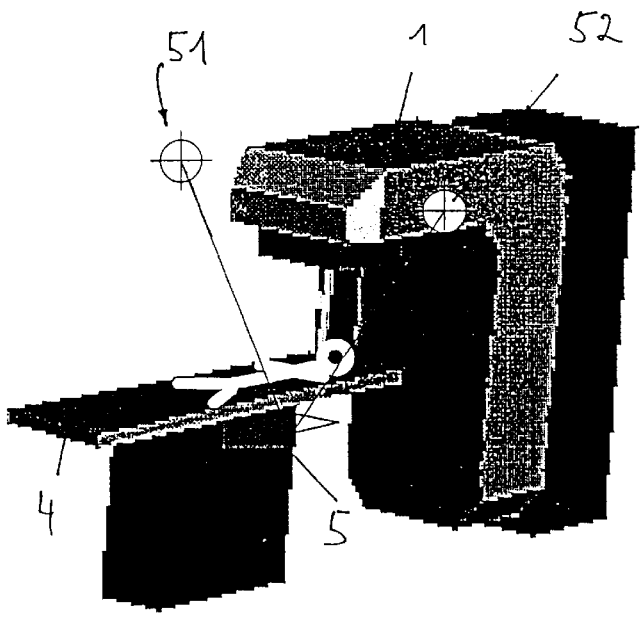
FIG. 6 is an illustration of the basic principle in producing X-ray images with separate X-ray sources.

FIG. 6 represents an alternative embodiment, in which not the linear accelerator itself, including the gantry 1, is used to produce the X-ray image in situ, but instead separate X-ray sources. These two separate X-ray sources for generating two X-ray images from different directions are indicated only schematically in FIG. 6, and are allocated the reference numerals 51 and 52. In front of these X-ray sources 51 and 52 too, markings may be applied, as described relative to FIG. 3, at a predetermined distance away, so that the exact position of the X-ray image on the imaging system 5 can always be mapped and the patient on the patient table 4 can be exactly repositioned once the positional error has been determined. Preferably, in this embodiment, the gantry does not need to be moved to produce the X-ray images.

In the foregoing description, preferred embodiments of the invention have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

What is claimed is:

1. A method for exact positioning of a patient for radiotherapy or radiotherapy comprising the steps:
   a) pre-positioning the patient relative to a linear accelerator,
   b) producing at least one X-ray image of the patient or one of his/her body parts in the vicinity of the radiation treatment target,
   c) mapping said X-ray image,
   d) generating at least one reconstructed image from a three-dimensional set of patient scanning data corresponding to said X-ray image,
   e) superimposing said reconstructed image and said X-ray image, and detecting the positional error electronically or computer-controlled on the basis of special landmarks in both images, and
   f) correcting the position of the patient on the basis of the detected positional error, and
   wherein pre-positioning is carried out by means of a computer-controlled and camera-controlled navigation and tracking system with the aid of artificial marker arrangements on the patient and on the treatment devices.

2. The method as set forth in claim 1, wherein at least two or more X-ray images and corresponding images are generated from different directions, and each are analyzed by comparison.

3. The method as set forth in claim 1, wherein said X-ray image is produced with the radiation source of said linear accelerator.

4. The method as set forth in claim 3, wherein said X-ray image is produced on an X-ray film.

5. The method as set forth in claim 3, wherein said X-ray image and/or said reconstructed image are output on a display.

6. The method as set forth in claim 5, wherein said superimposing of said X-ray image and of said reconstructed image occurs by manual marking and interleaving on a computer display.

7. The method as set forth in claim 3, wherein said X-ray image is produced on amorphous silicon.

8. The method as set forth in claim 1, wherein said X-ray image is produced by one, two or more separate X-ray sources.

9. The method as set forth in claim 1, wherein said X-ray image is produced on an image amplifier or detector.

10. The method as set forth in claim 1, wherein said superimposing of said X-ray image and of said reconstructed image occurs by computer-controlled automatic image fusion.

11. The method as set forth in claim 1, wherein said reconstructed image or images is/are generated as digitally reconstructed radiographs (DRRs), digitally composited radiographs (DCRs), MIP images, or as any two-dimensional image reconstruction from a set of three-dimensional patient scan data.

12. The method as set forth in claim 1, wherein the position of the patient is corrected by shifting a patient table.

13. The method as set forth in claim 1, wherein correcting the position of the patient occurs by operating said table manually.

14. The method as set forth in claim 12, wherein shifting of the patient table is automatically activated and corrected by a computer-controlled and camera-controlled navigation and tracking system with markers on the patient and/or patient table.

15. The method as set forth in claim 1, wherein, in the steps c) and d), a plurality of reconstructed images is generated, which are then superimposed electronically or computer-controlled, and compared to said mapped X-ray image until a reconstructed image is found which corresponds to said X-ray image, with the aid of which said positional error is then detected.

16. The method as set forth in claim 1, wherein the X-ray image is mapped by producing an X-ray image of the patient, detecting the three-dimensional position of the X-ray unit while producing the X-ray image, inserting markers in a predetermined or specific position relative to the X-ray source in the beam path thereof while producing the X-ray image, and calculating, from the geometry of the X-ray unit and from the position of the markers in the X-ray image, the precise three-dimensional imaging situation of the X-ray image.

17. The method as set forth in claim 1, wherein the reconstructed image is generated isocentrically.

18. The method as set forth in claim 1, wherein the marker arrangements include reflecting markers.

19. A method for exact positioning of a patient for radiotherapy or radiotherapy comprising the steps:
   a) pre-positioning the patient relative to a linear accelerator,
   b) producing at least one X-ray image of the patient or one of his/her body parts in the vicinity of the radiation treatment target, c) mapping said X-ray image, d) generating at least one reconstructed image from a three-dimensional set of patient scanning data corresponding to said X-ray image, e) superimposing said reconstructed image and said X-ray image, and detecting the positional error electronically or computer-controlled on the basis of special landmarks in both images, and f) correcting the position of the patient on the basis of the detected positional error, and wherein pre-positioning occurs by means of skin markers on the patient, natural landmarks or laser markings.

20. The method as set forth in claim 19, wherein the reconstructed image is generated isocentrically.

21. The method as set forth in claim 19, wherein at least two or more X-ray images and corresponding images are generated from different directions, and each are analyzed by comparison.

22. The method as set forth in claim 19, wherein said X-ray image is produced with the radiation source of said linear accelerator.

23. The method as set forth in claim 22, wherein said X-ray image is produced on an X-ray film.

24. The method as set forth in claim 22, wherein said X-ray image and/or said reconstructed image are output on a display.

25. The method as set forth in claim 22, wherein said superimposing of said X-ray image and of said reconstructed image occurs by manual marking and interleaving on a computer display.

26. The method as set forth in claim 19, wherein said X-ray image is produced on an image amplifier or detector.

27. The method as set forth in claim 19, wherein said X-ray image is produced on amorphous silicon.

28. The method, as set forth in claim 19, wherein said superimposing of said X-ray image and of said reconstructed image occurs by computer-controlled automatic image fusion.

29. The method as set forth in claim 19, wherein said reconstructed image or images is/are generated as digitally reconstructed radiographs (DRRs), digital composited radiographs (DCRs), MIP images, or as any two-dimensional image reconstruction from a set of three-dimensional patient scan data.

30. The method as set forth in claim 19, wherein the position of the patient is corrected by shifting a patient table.

31. The method as set forth in claim 30, wherein correcting the position of the patient occurs by operating said table manually.

32. The method as set forth in claim 19, wherein, in the steps c) and d), a plurality of reconstructed images is generated, which are then superimposed electronically or computer-controlled, and compared to said mapped X-ray image until a reconstructed image is found which corresponds to said X-ray image, with the aid of which said positional error is then detected.

33. The method asset forth in claim 19, wherein the X-ray image is mapped by producing an X-ray image of the patient, detecting the three-dimensional position of the X-ray unit while producing the X-ray image, inserting markers in a predetermined or specific position relative to the X-ray source in the beam path thereof while producing the X-ray image, and calculating, from the geometry of the X-ray unit and from the position of the markers in the X-ray image, the precise three-dimensional imaging situation of the X-ray image.

* * * * *